United States Patent
Saito et al.

(10) Patent No.: US 7,154,007 B2
(45) Date of Patent: Dec. 26, 2006

(54) LUMINOUS COMPOUNDS AND LABELING REAGENTS USING THE SAME

(75) Inventors: Michihiro Saito, Kashiwa (JP); Ernoe Pretsch, Ukikon am See (CH)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/491,788

(22) PCT Filed: Oct. 10, 2002

(86) PCT No.: PCT/JP02/10511

§ 371 (c)(1),
(2), (4) Date: Oct. 8, 2004

(87) PCT Pub. No.: WO03/033447

PCT Pub. Date: Apr. 24, 2003

(65) Prior Publication Data

US 2005/0033039 A1   Feb. 10, 2005

(30) Foreign Application Priority Data

Oct. 10, 2001   (JP)   ............... 2001-312562

(51) Int. Cl.
C07C 319/00 (2006.01)
C07C 49/00 (2006.01)
C07C 231/00 (2006.01)
C07C 233/00 (2006.01)
G01N 33/566 (2006.01)

(52) U.S. Cl. ............. 568/42; 568/331; 568/336; 564/143; 564/155; 564/308; 436/501

(58) Field of Classification Search ............. 568/42, 568/331, 336; 564/143, 155, 308; 436/501
See application file for complete search history.

(56) References Cited

U.S. PATENT DOCUMENTS 4,565,790 A * 1/1986 Hemmila et al. .......... 436/537

6,166,251 A    12/2000 Matsumoto et al. ....... 562/828
6,339,172 B1 * 1/2002 Matsui et al. ............. 562/828

FOREIGN PATENT DOCUMENTS

DE   2134000 A1   1/1972
EP   794174 A2   9/1997
WO   97/14679 A   4/1997
WO   01/38311 A   5/2001

OTHER PUBLICATIONS

Synthesis and Reactivity in Inorganic and Metal-Organic Chemistry, 1995, vol. 25, No. 5, M. Das et al, pp. 845-857.
Izvestiya Akademii Nauk SSSR, Seriya Khimicheskaya, 1986, No. 9, K. Paskevich et al, pp. 2125-2127.
Analytica Chimica Acta, 1981, vol. 130, No. 1, "Liquid-liquid extraction of gallium with bidentate ligands", E. Uhlemann et al, pp. 177-182.
Synthesis, 1994, No. 2, A.J. Baxter et al, pp. 207-211.
Penning, Thomas D. et al., "Synthesis and Biological Evaluation of the 1,5-Diarylpyrazole Class of Cyclooxygenase-2 Inhibitors: . . .", Journal of Medicinal Chemistry, 40(9), pp. 1347-1365, 1997, XP002358347.
Charles, Robert G. et al., "Fluorescent Europium Chelates Derived from Fluorinated . beta.-Diketones", Journal of Inorganic and Nuclear Chemistry, 29(3), 715-23, 1967, XP002358348.

* cited by examiner

*Primary Examiner*—Sikarl A. Witherspoon
(74) *Attorney, Agent, or Firm*—Mattingly, Stanger, Malur & Brundidge, P.C.

(57) ABSTRACT

This invention provides: a compound represented by formula (I):

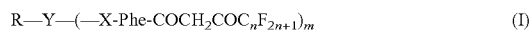

R—Y—(—X-Phe-COCH$_2$COC$_n$F$_{2n+1}$)$_m$   (I)

wherein R denotes hydrogen, alkyl, phenyl, or a group capable of binding to a protein, peptide, amino acid, nucleic acid, or nucleotide; Y denotes CH$_2$, a carbocyclic ring, or a heterocyclic ring; X denotes O, S, NH, CH$_2$, OCH$_2$, CONH, or NHCO; Phe denotes phenylene; n is an integer between 1 and 5; and m is 1, 2, or 3. This inventions also provides a luminous complex of such compound and a rare earth ion, a labeling reagent comprising such compound or luminous complex, and a process for labeling a protein, peptide, amino acid, nucleic acid, or nucleotide using such labeling reagent.

17 Claims, 11 Drawing Sheets

| PKNO | TIME | AREA | HEIGHT | MK | IDNO | CONC | NAME |
|---|---|---|---|---|---|---|---|
| 1 | 0.424 | 48189 | 22460 | V | | 0.0128 | |
| 2 | 0.562 | 52531212 | 33661866 | V | | 13.9575 | |
| 3 | 0.650 | 322889262 | 84899192 | SV | | 85.7912 | |
| 4 | 1.397 | 51926 | 17974 | TV | | 0.0138 | |
| 5 | 23.797 | 5337 | 689 | | | 0.0014 | |
| 6 | 23.825 | 5295 | 642 | V | | 0.0014 | |
| 7 | 24.122 | 8530 | 1337 | | | 0.0023 | |
| 8 | 24.286 | 826844 | 135538 | V | | 0.2197 | |
| | | 376366595 | 118739699 | | | 100.0000 | |

Amount injected 2ul
Flow rate 150 ul/min
Column CAPCELL PAK C18 UG120 3um 1.5mm*150mm
Detector 254 nm
Eluate CH3CN:H2O=3:1

| PKNO | NAME | TIME | MARK | CONC | AREA | HEIGHT |
|---|---|---|---|---|---|---|
| 1 | | 3.21 | | 99.331 | 33312302.99 | 1243512.4 |
| 2 | | 4.92 | | 0.217 | 72919.00 | 5414.5 |
| 3 | | 14.24 | | 0.452 | 151485.32 | 4364.7 |
| TOTAL | | | | 100.000 | 33536707.31 | 1253291.6 |

BFA

⑤

TTA

⑥

①

②

⑦ (BHHT)

③

* TTA : 4,4,4-Trifluoro-1-(2-thienyl)-1,3-butanedione
* BFA : 4,4,4-Trifluoro-1-phenyl-1,3-butanedione
* BHHT : 4,4'-bis(1",1",1",2",2",3",3"-heptafluoro-4",6"-hexanedion-6"-yl)-o-terphenyl

| | TRF #D1 | | F-4010 | | U-3300 | |
|---|---|---|---|---|---|---|
| | fluorescence intensity at $10^{-11}$ mol/mL | % vs BHHT | max Ex(nm) | peak intensity | max Abs(nm) | peak intensity |
| TTA | 346,464 | 34 | 348.8 | 1.458 | 329.0 | 0.381 |
| BFA | 228,316 | 22 | 337.6 | 1.278 | 323.5 | 0.254 |
| 1 | 256,477 | 25 | 336.0 | 1.250 | 333.5 | 0.235 |
| 2 | 543,166 | 53 | 347.2 | 3.192 | nd | nd |
| 3 | 264,518 | 26 | nd | nd | nd | nd |
| 4 | 1,268,801 | 123 | 336.0 | 6.009 | 348.5 | 1.274 |
| 5 | 291,146 | 28 | 337.2 | 1.822 | 341.0 | 0.476 |
| 6 | 557,028 | 54 | 329.0 | 2.108 | 337.5 | 1.036 |
| 7(BHHT) | 1,028,165 | 100 | 344.8 | 5.723 | 340.0 | 1.104 | nd: not-done

| 1/2 life time | |
|---|---|
| chelate | (msec) |
| TTA | 0.69 |
| BFA | 0.66 |
| 1 | 0.62 |
| 4 | 0.69 |
| 5 | 0.65 |
| 6 | 0.56 |
| 7(BHHT) | 0.67 |
| Plate | 0.33 |

Minimal detection sensitivity

| LDL (3SD) | pg/mL |
|---|---|
| TTA | NA |
| BFA | NA |
| 1 | NA |
| 2 | 3.3 |
| 3 | 490.4 |
| 4 | 0.5 |
| 5 | 3.6 |
| 6 | 1.9 |
| 7(BHHCT) | 2.6 |

NA: not-available

LUMINOUS COMPOUNDS AND LABELING REAGENTS USING THE SAME

This application is the national stage of PCT/JP02/10511, filed Oct. 10, 2002, and published as WO 03/033447 on Apr. 24, 2003.

TECHNICAL FIELD

The present invention relates to a compound for a labeling reagent suitable for use in time-resolved fluorometry, delayed phosphorimetry, or fluorescence resonance energy transfer assay employed in nucleic acid assay, immunoassay, and chemiluminescence assay. More particularly, the present invention relates to a compound that is capable of emitting fluorescence, delayed fluorescence, or phosphorescence when it becomes a complex through coordinate bonding with metal ions.

BACKGROUND ART

Immunoassays or nucleic acid assays are carried out by a variety of means including visual and radioactivity analyses. Fluorescence intensities of fluorophores or substances labeled with fluorescent dyes are often measured because of the simplicity of the procedure. This technique is useful because the wavelength of the generated fluorescence or luminescence is in a range that is different from that of the excitation light, and can thus be accurately detected. Fluorescence or luminescence, however, disappears in a relatively short period of time, this enables the fluorescence or luminescence to be detected at substantially the same time as the generation of the excitation light, so that noises generated by the excitation light are also detected, and the background noises are sometimes heightened.

Peaks of the fluorescence or emission wavelength often exist in wavelength ranges that are longer than the peaks of the excitation wavelength. Fluorescence or emission is separated from the excitation light using, for example, a filter for selecting a wavelength and then its intensity is measured. The difference between the excitation wavelength and the emission or fluorescence wavelength is generally referred to as a Stokes shift. In fluorescence assays, a Stokes shift is small. Thus, it is sometimes difficult to distinguish the excitation light from the fluorescence emission based on differences in wavelengths.

Fluorescent dyes such as rhodamine and fluoresceine have wide fluorescence wavelength distributions, therefore broad fluorescence waveforms can be obtained. When simultaneous detections of several substances using several fluorophores or fluorescent dyes are intended, it is difficult to assay individual substances due to the overlapping fluorescence wavelength regions. Alternatively, this assay requires the application of a conversion formula to analyze the algorithm in order to find out the amount of each substance.

Chemiluminescence techniques including electrochemiluminescence technique and enzymatic chemiluminescence technique are sometimes employed as techniques in which excitation lights do not interfere with the emission light. In these techniques, labeled bodies or labeling dyes are not irradiated with the excitation light, and thus, the light emission only is detected. A technique has been developed in which isoluminol or acridium ester is labeled to detect the object substance. Another technique involves a highly-sensitive assay system that utilizes reactions between peroxidase and luminol in which the enzyme is employed as a labeling substance and this labeling substance allows a substrate to emit light, or reactions between adamantyl 1,2-dioxetane arylphosphate (AMPPD) and alkali phosphatase.

Fluorescence or phosphorescence of a complex comprising a rare earth element, such as europium or samarium, and a ligand thereof has a long lasting light emission. Recently, time-resolved fluorometry or phosphorimetry that makes use of this advantage has been developed as an excellent technique. Properties, such as a long period of fluorescence or phosphorescence being quenched, a large Stokes shift, and sharp peak waveforms of fluorescence and phosphorescence, enable the detection of fluorescent or phosphorescent signals while excluding noises caused by the excitation light. Thus, a highly sensitive analytical technique can be provided. In this technique, the excitation light is applied via a xenon flash lamp or laser beam while pulsing, and the fluorescence or phosphorescence of interest is detected after the fluorescence of the apparatus or other substances caused by the excitation lights disappears. This ligand is improved, and compounds such as 4,7-bis(chlorosulfophenyl)-1,10-phenanthroline-2,9-dicarboxylic acid (BCPDA) or 4,4'-bis(1",1",1",2",2",3",3"-heptafluoro-4",6"-hexanedion-6"-yl) chlorosulfo-o-terphenyl (BHHCT) have been reported. BHHCT is disclosed in, for example, JP-A-09-241233. These are excellent chelate compounds, although they are not yet improved enough to yield the minimal detection sensitivity required for immunoassays or nucleic acid assays.

DISCLOSURE OF THE INVENTION

The present invention relates to labeling reagents suitable for use in time-resolved fluorometry, delayed phosphorimetry, or fluorescence resonance energy transfer assay employed in nucleic acid assay, immunoassay, and chemiluminescence assay. An object of the present invention is to provide a useful labeling reagent that can detect a substance of interest in a sample with high sensitivity and a compound suitably used in a labeling reagent.

The present invention includes the following inventions.

(1) A compound represented by formula (I):

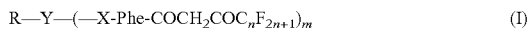

R—Y—(—X-Phe-COCH$_2$COC$_n$F$_{2n+1}$)$_m$  (I)

wherein R denotes hydrogen, alkyl, phenyl, or a group capable of binding to a protein, peptide, amino acid, nucleic acid, or nucleotide; Y denotes CH$_2$, a carbocyclic ring, or a heterocyclic ring; X denotes O, S, NH, CH$_2$, OCH$_2$, CONH, or NHCO; Phe denotes phenylene; n is an integer between 1 and 5; and m is 1, 2, or 3.

(2) The compound according to (1) above represented by formula (1):

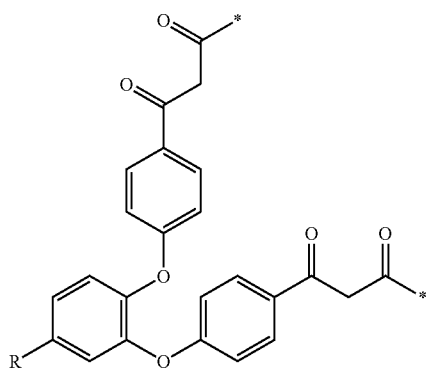

wherein * denotes C$_n$F$_{2n+1}$ (wherein n is an integer between 1 and 5) and R is as defined in (1) above.

(3) The compound according to (1) above represented by formula (2):

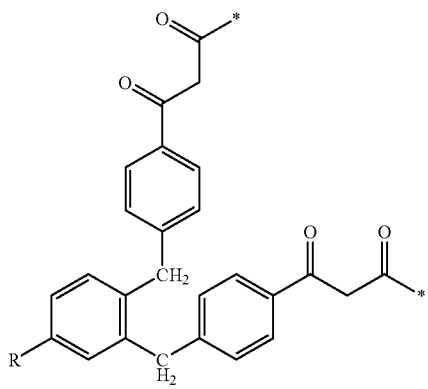

wherein * denotes $C_nF_{2n+1}$ (wherein n is an integer between 1 and 5) and R is as defined in (1) above.

(4) The compound according to (1) above represented by formula (3):

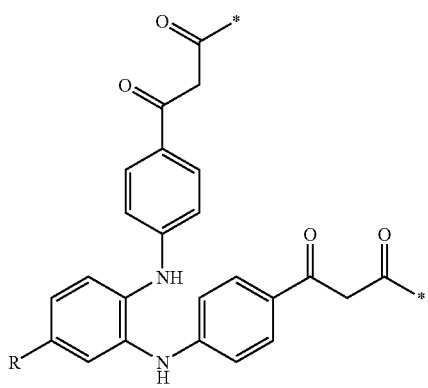

wherein * denotes $C_nF_{2n+1}$ (wherein is an integer between 1 and 5) and R is as defined in (1) above.

(5) The compound according to (1) above represented by formula (4):

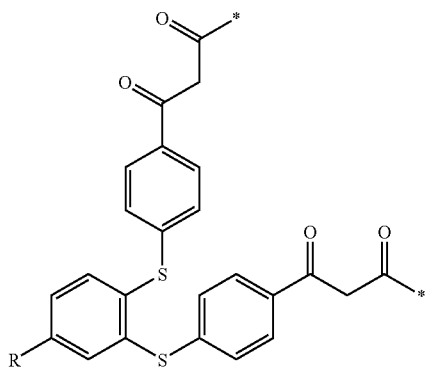

wherein * denotes $C_nF_{2n+1}$ (wherein n is an integer between 1 and 5) and R is as defined in (1) above.

(6) The compound according to (1) above represented by formula (5):

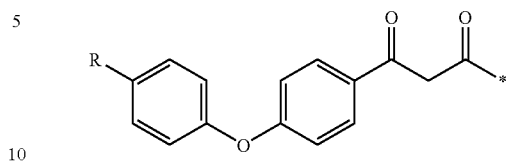

wherein * denotes $C_nF_{2n+1}$ (wherein n is an integer between 1 and 5) and R is as defined in (1) above.

(7) The compound according to (1) above represented by formula (6):

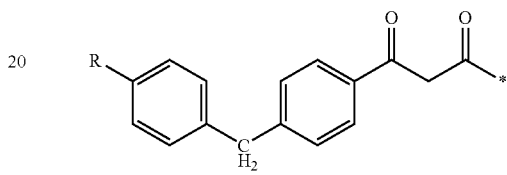

wherein * denotes $C_nF_{2n+1}$ (wherein n is an integer between 1 and 5) and R is as defined in (1) above.

(8) The compound according to (1) above represented by formula (7):

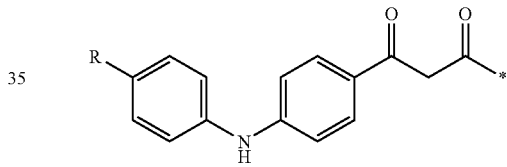

wherein * denotes $C_nF_{2n+1}$ (wherein n is an integer between 1 and 5) and R is as defined in (1) above.

(9) The compound according to (1) above represented by formula (8):

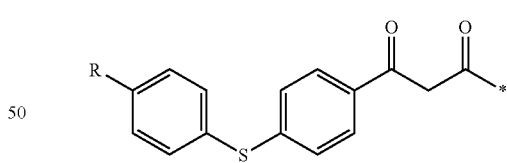

wherein * denotes $C_nF_{2n+1}$ (wherein n is an integer between 1 and 5) and R is as defined in (1) above.

(10) The compound according to (1) above represented by formula (9):

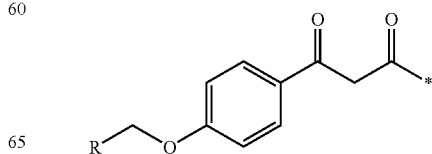

wherein * denotes $C_nF_{2n+1}$ (wherein n is an integer between 1 and 5) and R is as defined in (1) above.

(11) The compound according to (1) above represented by formula (10):

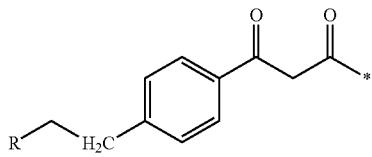

wherein * denotes $C_nF_{2n+1}$ (wherein n is an integer between 1 and 5) and R is as defined in (1) above.

(12) The compound according to (1) above represented by formula (11):

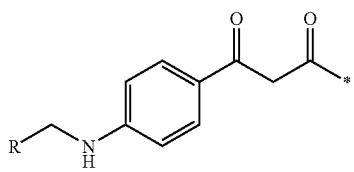

wherein * denotes $C_nF_{2n+1}$ (wherein n is an integer between 1 and 5) and R is as defined in (1) above.

(13) The compound according to (1) above represented by formula (12):

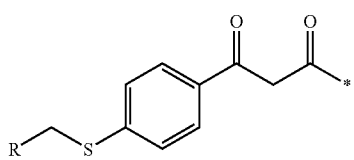

wherein * denotes $C_nF_{2n+1}$ (wherein n is an integer between 1 and 5) and R is as defined in (1) above.

(14) The compound according to (1) above represented by formula (13):

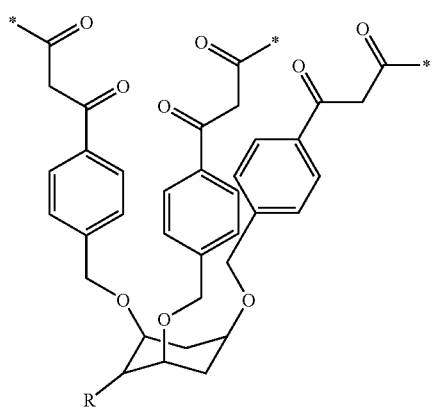

wherein * denotes $C_nF_{2n+1}$ (wherein n is an integer between 1 and 5) and R is as defined in (1) above.

(15) The compound according to (1) above represented by formula (14):

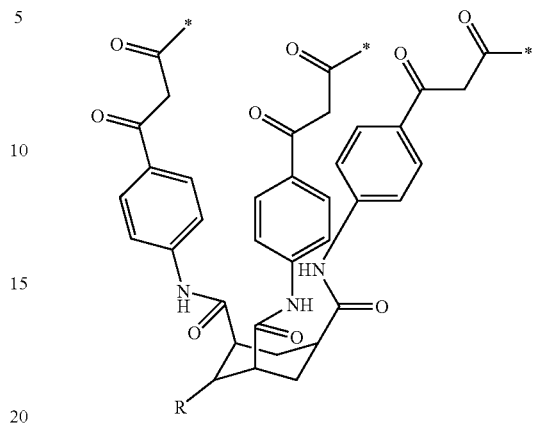

wherein * denotes $C_nF_{2n+1}$ (wherein n is an integer between 1 and 5) and R is as defined in (1) above.

(16) The compound according to any of (1) to (15) above, wherein R denotes a group in which a functional group capable of binding to a protein, peptide, amino acid, nucleic acid, or nucleotide is bound to a terminus of a spacer comprising a carbon chain that may optionally contain, as a member of this chain, at least one hetero atom selected from among oxygen, nitrogen, and sulfur.

(17) The compound according to any one of (1) to (16) above, wherein R comprises at least one functional group represented by the following formulae:

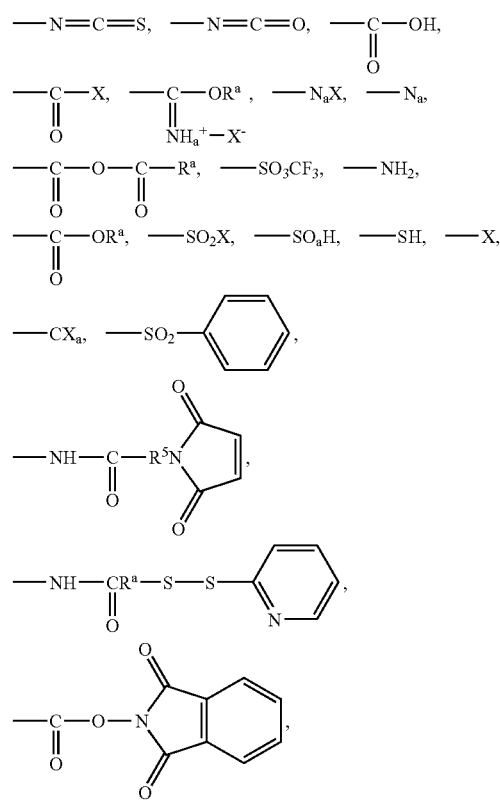

-continued

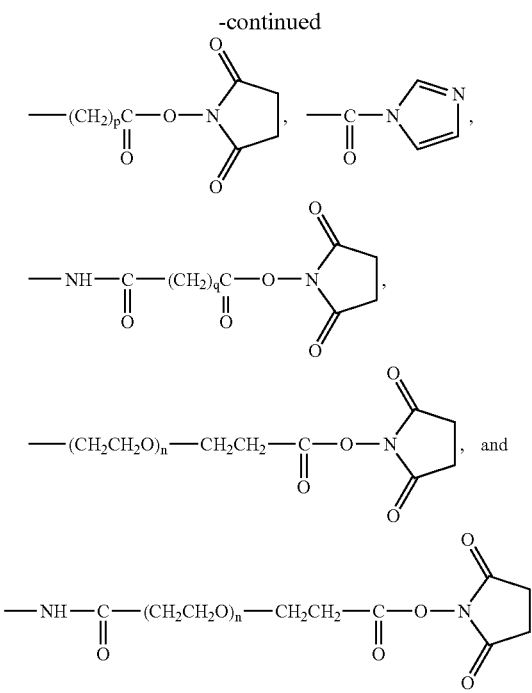

wherein X is selected from among a halide atom, —OSO₃CH₃, —OSO₂F, —OSO₂CF₃, —SO₂C₄F₉, and

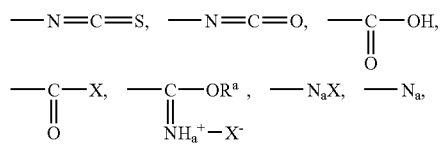

$R^A$ is selected from among alkyl, alkenyl, aryl, and aralkyl; $R^B$ is selected from among alkylene, arylene, and aralkylene; p is an integer between 0 and 5, inclusive; q is an integer between 2 and 10, inclusive; and n is an integer between 1 and 20, inclusive.

(18) A fluorescent complex comprising the compound according to any one of (1) to (17) above and a rare earth ion.

(19) A labeling reagent comprising the compound according to any one of (1) to (17) above or the fluorescent complex according to (18) above.

(20) The labeling reagent according to (19) above for immunoassays or nucleic acid assays.

(21) A method for labeling a protein, peptide, amino acid, nucleic acid, or nucleotide utilizing the labeling reagent according to (19) or (20) above.

In formula (I), R denotes hydrogen, alkyl, phenyl, or a group capable of binding to a protein, peptide, amino acid, nucleic acid, or nucleotide. The "group capable of binding to a protein, peptide, amino acid, nucleic acid, or nucleotide" used herein is not particularly limited as long as it is capable of binding to any of the amino, carboxyl, mercapto, or hydroxyl group existing in a target protein, peptide, amino acid, nucleic acid, or nucleotide. Examples thereof include groups having at least one functional group represented by the following formulae:

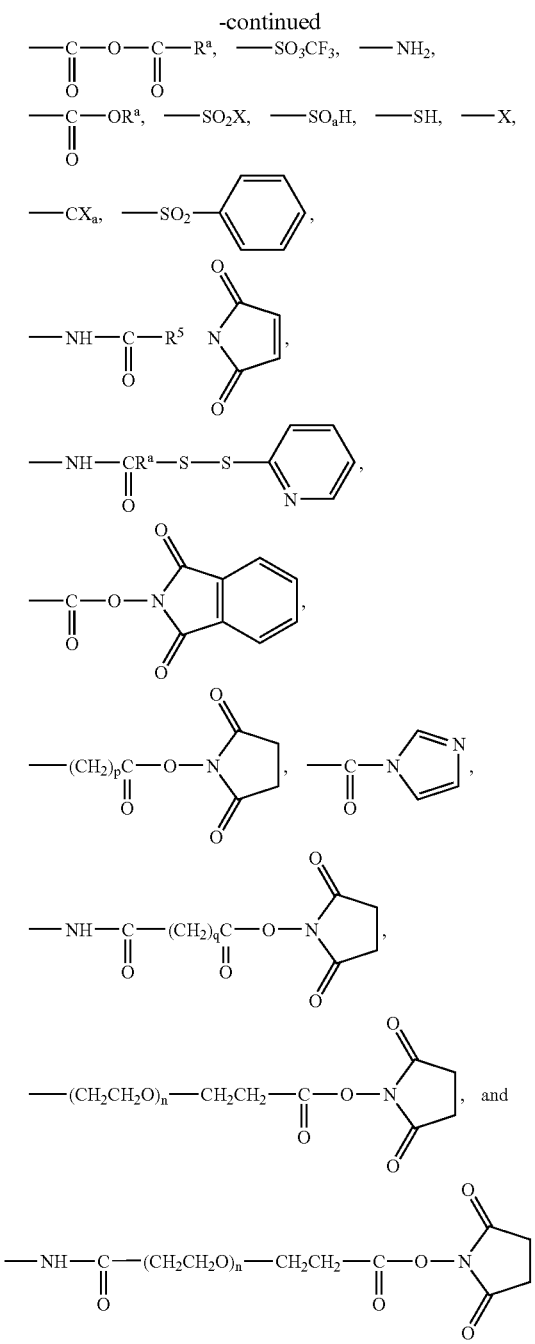

wherein X is selected from among a halide atom, —OSO₃CH₃, —OSO₂F, —OSO₂CF₃, —SO₂C₄F₉, and

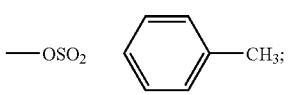

$R^A$ is selected from among alkyl, alkenyl, aryl, and aralkyl; $R^B$ is selected from among alkylene, arylene, and aralkylene; p is an integer between 0 and 5, inclusive; q is an integer between 2 and 10, inclusive; and n is an integer between 1 and 20, inclusive.

In the above formulae, a halide atom (halogen atom) denoted by X is either fluoride (fluorine), chloride (chlorine), bromide (bromine), or iodide (iodine). Concerning groups denoted by $R^A$, for example, alkyl is $C_{1-6}$ alkyl (e.g., methyl or ethyl), alkenyl is $C_{2-6}$ alkenyl (e.g., vinyl or propenyl), aryl is phenyl or naphthyl, and aralkyl is benzyl, phenethyl, or naphthylmethyl. Concerning groups denoted by $R^B$, for example, alkylene is $C_{1-6}$ alkylene (e.g., $—(CH_2)_n—$ wherein n is an integer between 1 and 6), arylene is phenylene or naphthylene, and aralkylene is $—Ar—(CH_2)_n—$ wherein Ar is phenylene or naphthylene and n is an integer between 1 and 6.

When R is a group capable of binding to a protein, peptide, amino acid, nucleic acid, or nucleotide, the protein, peptide, amino acid, nucleic acid, or nucleotide to which R is bound is not particularly limited. Examples thereof include antibodies, labeled antibodies, antigens, biotin, avidin, streptavidin, bovine serum albumin, hapten, hormone, polypeptide, and polynucleotide.

Examples of carbocyclic rings denoted by Y include an optionally substituted aromatic monocyclic hydrocarbon (e.g., a benzene ring), a 3- to 8-membered ring comprising an optionally-substituted saturated monocyclic hydrocarbon (e.g., a cyclohexane ring), a 4- to 8-membered ring comprising an optionally substituted unsaturated monocyclic hydrocarbon (e.g., a cyclohexene or cyclopentadiene ring), an optionally substituted fused polycyclic hydrocarbon (e.g., a naphthalene, phenanthrene, or fluorene ring), and a hydrocarbon ring complex (e.g., a biphenyl, terphenyl, phenanthrene, or fluorene ring).

Examples of heterocyclic rings denoted by Y include an optionally substituted aromatic heterocyclic ring (e.g., a thiophene ring), an optionally substituted 3- to 8-membered saturated heterocyclic ring (e.g., a tetrahydrofuran ring), an optionally unsaturated heterocyclic ring (a pyroline ring), and an optionally substituted fused heterocyclic ring (e.g., a benzothiophen, dibenzothiophene, benzofuran, or dibenzofuran ring).

Phenylene denoted by Phe is preferably 1,4-phenylene.

The rare earth ion used in the present invention is preferably a lanthanoid ion, and examples thereof include europium (Eu), samarium (Sm), terbium (Tb), and dysprosium (Dy) ions.

The molecular size of a chelate compound comprising a metal element is relatively small. A peptide or amino acid, particularly a protein or nucleotide chain, labeled via a chain (spacer) mainly composed of carbon (C) may be more advantageous. A protein or nucleotide chain often has a complicated three-dimensional structure, and a binding site of a label with a functional group sometimes exists inside this structure. Use of a spacer is effective when these substances are intended to be labeled.

An example of the aforementioned spacer is a spacer comprising a carbon chain that may optionally contain, as a member of this chain, at least one hetero atom selected from among oxygen, nitrogen, and sulfur.

A specific example of R comprising the aforementioned spacer is represented by the formula:

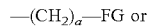

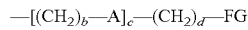

wherein a is an integer between 1 and 40; b is an integer between 1 and 20; c is an integer between 1 and 10; d is an integer between 0 and 20; A denotes oxygen (O), nitrogen (NH), or sulfur (S); and FG denotes a functional group.

Fluorescence is generated at the time of transition from the first excited state to the ground state, and phosphorescence is generated at the time of transition from one state to another state having different spin multiplicity. In the past, a labeling reagent having a β-diketone structure and a labeling reagent having an aromatic group existed as complex reagents coordinately bonded to heavy metal ions. Fluorescein bridged with —O— (oxygen) exhibits intensive fluorescence or phosphorescence whereas emission of fluorescence or phosphorescence is not observed in the case of phenolphthalein. Quinoline to which a benzene ring had been applied exhibits fluorescence or phosphorescence while no fluorescence or phosphorescence is observed in the case of pyridine.

When the intensity of fluorescence or phosphorescence is intended to be enhanced, a spacer that has both an aromatic group and O (oxygen), that is stable, and that yields high efficiency of synthesis is advantageously used.

In immunoassays or nucleic acid assays, a solid phase is utilized as a platform for reaction, upon which a product of antigen-antibody reaction or a product of DNA or RNA hybridization is formed, and the resultant is then assayed. A label or labeling dye is first bound to an antigen, antibody, DNA, or RNA to compose the reaction product. Alternatively, it is allowed to bind to a reaction product at the final stage with the utilization of, for example, reactions between avidin and biotin, and measurement is then initiated.

The compound and the labeling reagent of the present invention have a β-diketone structure and an aromatic group. They are comprised of O, S, NH, $CH_2$, $OCH_2$, CONH, or NHCO denoted by X between phenylene denoted by Phe and $CH_2$, a carbocyclic ring, or a heterocyclic ring denoted by Y. This construction enlarges the range of motion of the compound and the labeling reagent at the β-diketone site for bridging rare earth elements, exemplified by europium, and rare earth ions can be more effectively sustained. Thus, rare earth ions are more steadily coordinately bound with the β-diketone site. Accordingly, fluorescence or phosphorescence can be certainly emitted when irradiated with adequate excitation light.

The compound and the labeling reagent of the present invention are comprised of O, S, NH, $CH_2$, $OCH_2$, CONH, or NHCO denoted by X between phenylene denoted by Phe and a carbocyclic or heterocyclic ring denoted by Y as mentioned above. This construction allows an aromatic group (phenylene group) to be located discontinuously from a carbocyclic or heterocyclic ring. Thus, an effective chelate compound can be obtained without significantly inhibiting hydrophilic properties.

The compound and the labeling reagent of the present invention are comprised of O, S, NH, $CH_2$, $OCH_2$, CONH, or NHCO denoted by X between phenylene denoted by Phe and a carbocyclic or heterocyclic ring denoted by Y. Because of this construction, the compound and the labeling reagent of the present invention are less likely to be affected by the electronic absorption effects at sites where they counter $C_nF_{2n+1}$ (wherein n is an integer between 1 and 5) and the β-diketone site. This facilitates the introduction of reactive groups. Accordingly, conjugates thereof with an amino acid, peptide, protein, or nucleic acid can be more efficiently obtained.

The compound and the labeling reagent of the present invention are comprised of O, S, NH, $CH_2$, $OCH_2$, CONH, or NHCO denoted by X between phenylene denoted by Phe and a carbocyclic or heterocyclic ring denoted by Y. Because of this construction, when the compound and the labeling reagent of the present invention are allowed to bind to solid phase carriers such as amino acids, peptides, proteins, nucleic acids, or plastic particles via a reactive group, the compound and the labeling reagent become less likely to be affected by these substances at the β-diketone site and they can effectively sustain rare earth ions. Thus, rare earth ions can be more steadily coordinately bound with the β-diketone site. This enables the emission of certain fluorescence or phosphorescence when irradiated with adequate excitation light.

Further, when the compound and the labeling reagent of the present invention employ a spacer in R, the functional group of R becomes more likely to bind to a protein, nucleotide chain, or the like. This can increase the number of labels per molecule of the labeled substance.

The compound of the present invention can be produced, for example, in the following manner.

(Production Process 1)

The First Step

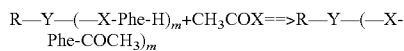
R—Y—(—X-Phe-H)$_m$+CH$_3$COX==>R—Y—(—X-Phe-COCH$_3$)$_m$ wherein X denotes a halogen atom, such as chlorine, and R, Y, X, and Phe are as defined in (I) above.

This reaction is so-called Friedel-Crafts acylation and it can be carried out in accordance with a conventional technique. Dichloromethane, chloroform, or the like is used as a solvent, and reaction is carried out in the presence of a Lewis acid such as aluminum chloride.

The Second Step

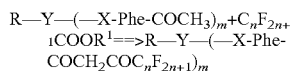
R—Y—(—X-Phe-COCH$_3$)$_m$+C$_n$F$_{2n+1}$COOR$^1$==>R—Y—(—X-Phe-COCH$_2$COC$_n$F$_{2n+1}$)$_m$ wherein R$^1$ denotes lower alkyl, such as methyl or ethyl, and R, Y, X, Phe, n, and m are as defined in (I) above.

This reaction is the condensation of a ketone compound and an ester compound, and it can be carried out in accordance with any conventional technique. Cyclohexane, n-hexane, diethyl ether, or the like is used as a solvent, and reaction is carried out in the presence of sodium hydride, metalalkoxide, or the like.

(Production Process 2)

This production process is employed when X denotes CH$_2$.

The First Step

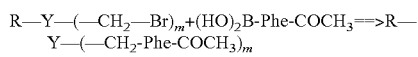
R—Y—(—CH$_2$—Br)$_m$+(HO)$_2$B-Phe-COCH$_3$==>R—Y—(—CH$_2$-Phe-COCH$_3$)$_m$ wherein R, Y, Phe, and m are as defined in (I) above.

This reaction is carried out in the presence of PdCl$_2$(dppf).CH$_2$Cl$_2$(dppf=1,1'-bis(diphenylphosphino)ferrocene) in a solvent such as a mixed solvent of tetrahydrofuran and water.

The Second Step

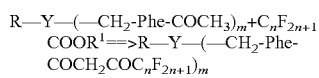
R—Y—(—CH$_2$-Phe-COCH$_3$)$_m$+C$_n$F$_{2n+1}$COOR$^1$==>R—Y—(—CH$_2$-Phe-COCH$_2$COC$_n$F$_{2n+1}$)$_m$ wherein R$^1$ denotes lower alkyl, such as methyl or ethyl, and R, Y, Phe, n, and m are as defined in (I) above.

This reaction can be carried out in the same manner as with the second step of Production Process 1.

(Production Process 3)

This production process is employed when X denotes O.

The First Step

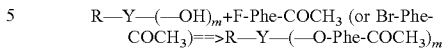
R—Y—(—OH)$_m$+F-Phe-COCH$_3$ (or Br-Phe-COCH$_3$)==>R—Y—(—O-Phe-COCH$_3$)$_m$ wherein R, Y, Phe, and m are as defined in (I) above.

This reaction is carried out by adding K$_2$CO$_3$, NaOH, NaH, or the like to a solvent.

The Second Step

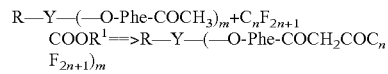
R—Y—(—O-Phe-COCH$_3$)$_m$+C$_n$F$_{2n+1}$COOR$^1$==>R—Y—(—O-Phe-COCH$_2$COC$_n$F$_{2n+1}$)$_m$ wherein R$^1$ denotes lower alkyl, such as methyl or ethyl, and R, Y, Phe, n, and m are as defined in (I) above.

This reaction can be carried out in the same manner as with the second step of Production Process 1.

The thus obtained compounds can be used as labeling reagents for proteins, peptide, amino acids, nucleic acids, or nucleotides. Alternatively, they can be used by being immobilized onto the surfaces of carriers such as plastic particles or being included in hollow bodies such as liposomes.

Labeling reactions utilizing the compound of the present invention can be carried out by selecting suitable reactions in accordance with the correlation between the functional group in the compound and a functional group in a protein or nucleic acid. For example, labeling can be carried out by amide formation between chlorosulfonyl or carboxyl in the compound of the present invention and an amino group in the protein. This amide formation easily proceeds in a carbonate buffer or Tris-HCl buffer (pH: between 9.0 and 9.5) at room temperature.

Examples of immunoassays utilizing the labeling reagent of the present invention are time-resolved fluoroimmunoassays and specific binding assays utilizing antigen-antibody reactions. The term "time-resolved fluoroimmunoassays" refers to highly sensitive fluoroimmunoassays in which only the fluorescent signals of the label are subjected to time-resolved fluoroassays using a long-lived fluorescent label (e.g., Eu-chelate) after the short-lived background fluorescence disappeared. The term "specific binding assays" refers to, for example, immunoassays utilizing antigen-antibody reactions, assays utilizing a receptor-acceptor bond, or assays utilizing nucleic acid hybridization.

This description includes part or all of the contents as disclosed in the description and/or drawings of Japanese Patent Application No. 2001-312562, which is a priority document of the present application.

BEST MODES FOR CARRYING OUT THE INVENTION

The present invention is hereafter described in detail with reference to the following examples, although the technical scope of the present invention is not limited to these examples.

EXAMPLE 1

The following is an embodiment of a process for synthesizing a compound represented by formula (6).

The First Step
The following is the first step.

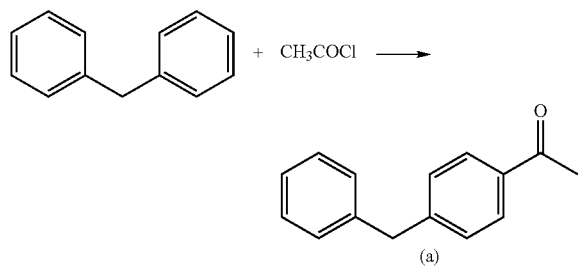

Materials
(1) Anhydrous aluminum chloride: 2.18 g
(2) Anhydrous dichloromethane: 35 ml
(3) Acetyl chloride: 1.29 g
(4) Diphenylmethane: 2.5 g Process of Synthesis Materials (1) and (2) were added to a flask, and the content therein was cooled to 0° C. Material (3) was further added thereto, 15 ml of a dichloromethane solution of material (4) was slowly added dropwise under cooling, and the mixture was stirred at room temperature for 2 hours. Ice (approximately 15 g) was added to the mixture, 20 ml of 1N HCl solution was further added, the precipitated aluminum oxide was allowed to dissolve, and an organic layer was fractionated. An aqueous layer was extracted three times with 20 ml of dichloromethane. The organic layer was mixed and rinsed. Anhydrous magnesium sulfate was added, a solvent was removed by distillation under reduced pressure, and a residue was purified by silica gel chromatography (solvent: n-hexane:ethyl acetate=3:2) to obtain Compound (a) (yield: 96%).

The Second Step
The following is the second step.

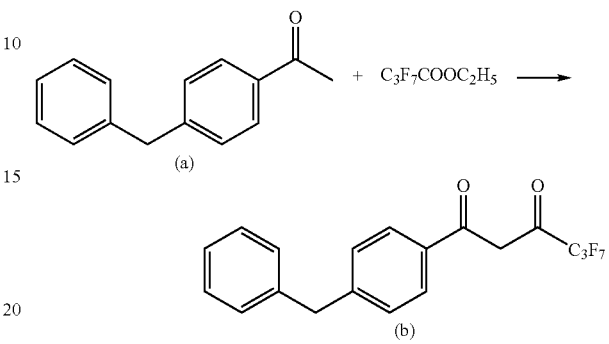

Materials
(1) Sodium hydride (60% in oil): 60 mg
(2) Anhydrous cyclohexane: 5 ml
(3) $C_3F_7COOC_2H_5$: 460 mg
(4) Compound (a): 200 mg Process of Synthesis Materials (1) and (2) were added to a flask, materials (3) and 3 ml of a cyclohexane solution (material (4)) were added thereto while heating and stirring, and the mixture was further stirred at room temperature for 30 minutes. An aqueous solution of 15% acetic acid was added to the mixture, and the resultant was added to 10 ml of ice water. An organic layer was fractionated with the aid of a separatory funnel, and an aqueous layer was extracted three times with 20 ml of diethyl ether. An organic layer was mixed, rinsed, and dried over anhydrous magnesium sulfate. A solvent was removed by distillation under reduced pressure, and a residue was purified by silica gel column chromatography (solvent: n-hexane:ethyl acetate=3:2) to obtain light yellow Compound (b) (yield: 99%).

Figure 1:
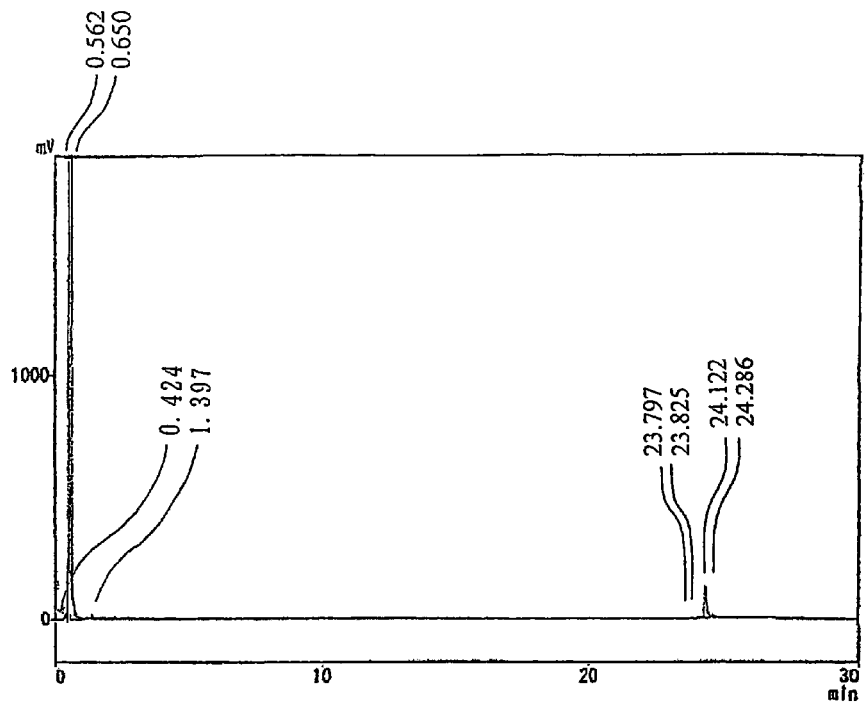
FIG. 1 shows the results of gel chromatography analysis of Compound (b) obtained in Example 1.

FIG. 1 shows the results of gel chromatography analysis of Compound (b). The m/z value of Compound (b) was found to be 406 as a result of TOF/MF spectrum analysis.

EXAMPLE 2

The following is an embodiment of a process for synthesizing a compound represented by formula (2).

The First Step
The following is the first step.

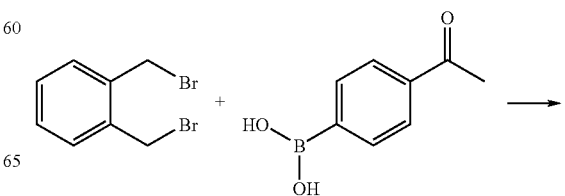

-continued

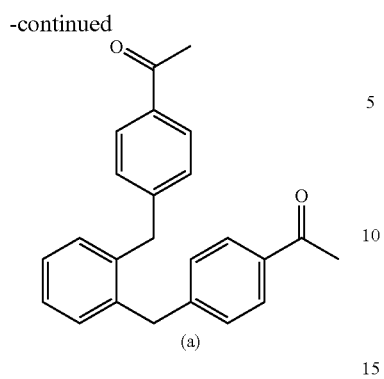

(a)

Materials
(1) 1,2-Bis(bromomethyl)benzene: 5.0 g
(2) 4-Acetylphenylboronic acid: 13.6 g
(3) A mixed solution of tetrahydrofuran (THF, 50 ml) and distilled water (5 ml)
(4) Cesium carbonate: 18.5 g
(5) $PdCl_2(dppf).CH_2Cl_2$: 1.5 g
 dppf=1,1'-Bis(diphenylphosphino)ferrocene
Reaction temperature: 70° C. (reflux)
Reaction period: 1 day Process of Synthesis Materials (1), (2), (3), and (4) were mixed in a reaction vessel, and the resultant was stirred while heating at 70° C. Material (5) was added thereto 30 minutes later. Heating was terminated 24 hours later, and the reaction solution was added to 60 ml of distilled water, followed by extraction with 80 ml of chloroform. The organic layer was washed with 40 ml of an aqueous solution of 5% hydrochloric acid and 40 ml of distilled water in that order and then dried over magnesium sulfate. The solvent was removed by distillation under reduced pressure, and 6 g of a crude product was obtained. After the product was separated and purified by silica gel chromatography, it was further fractionated and purified by gel chromatography. Thus, 1.0 g of Compound (a) was obtained (HPLC purity: 99%, yield: 15%).

$^1$H NMR (300 MHz, $CDCl_3$) δ 2.56 (6H, s), 3.96 (4H, s), 7.10–7.15 (6H, m), 7.23–7.27 (2H, m), 7.81–7.84 (4H, m)

MS (MALDI TOF) m/z 344 (M+H$^+$)

The Second Step

The following is the second step.

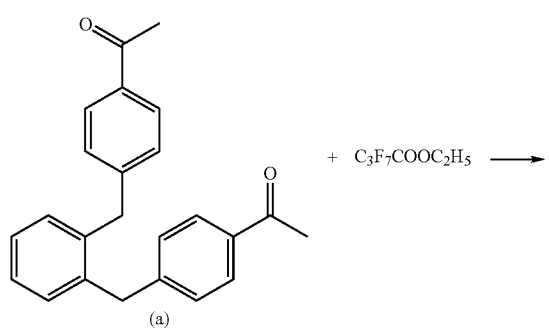

+ $C_3F_7COOC_2H_5$ →

(a)

-continued

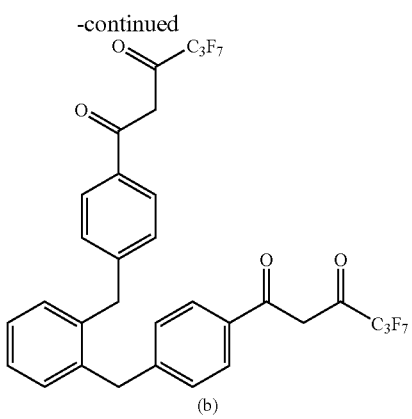

(b)

Materials
(1) Compound (a): 300 mg
(2) $C_3F_7COOC_2H_5$: 440 mg
(3) Anhydrous diether ether: 12 ml
(4) Sodium methoxide: 99 mg
Reaction temperature: room temperature
Reaction period: 1 day Process of Synthesis Materials (1), (2), (3), and (4) were mixed in a reaction vessel. An aqueous solution of 10% sulfuric acid (12 ml) was added thereto 24 hours later. After the mixture was stirred for 15 minutes, the organic layer was removed by distillation under reduced pressure, and the precipitated crystal was filtered. After the crystal was thoroughly rinsed, it was added to 10 ml of ethanol, followed by stirring while heating. Ethanol was removed by distillation under reduced pressure until the volume thereof became approximately 5 ml, 20 ml of petroleum ether was added thereto, and the mixture was stirred while heating. Insoluble matters were filtered, and the solvent was removed by distillation. Thus, 300 mg of Compound (b) was obtained. The compound was fractionated and purified by gel chromatography to obtain 100 mg of Compound (b).

MS (MALDI TOF) m/z 735 (M+H$^+$)

Figure 2:
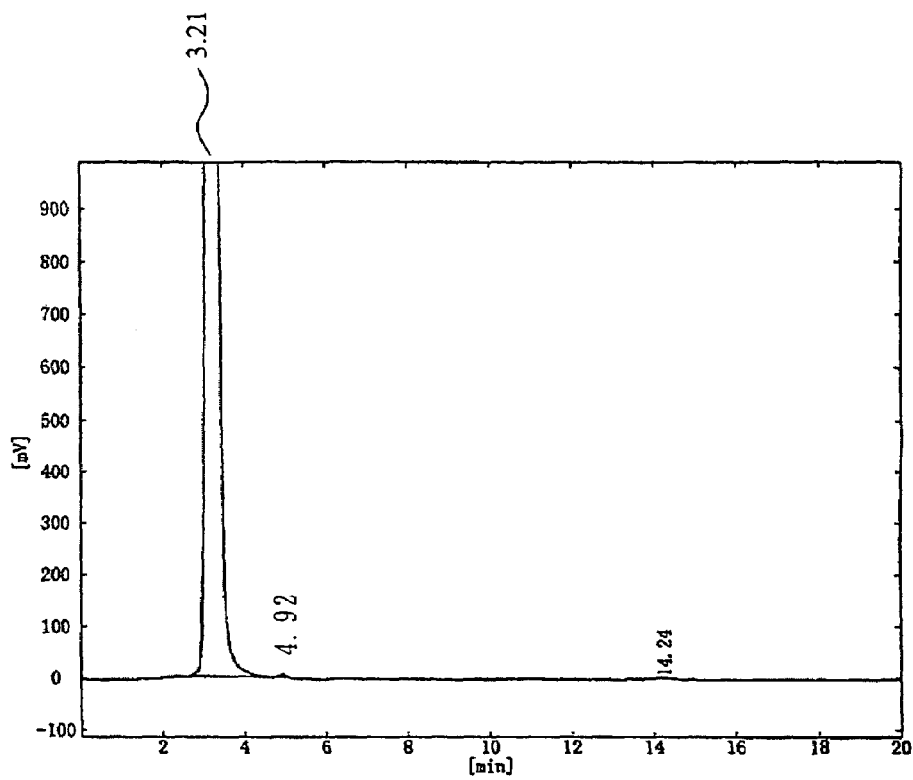
FIG. 2 shows the results of HPLC analysis of Compound (b) obtained in Example 2.
Figure 3:
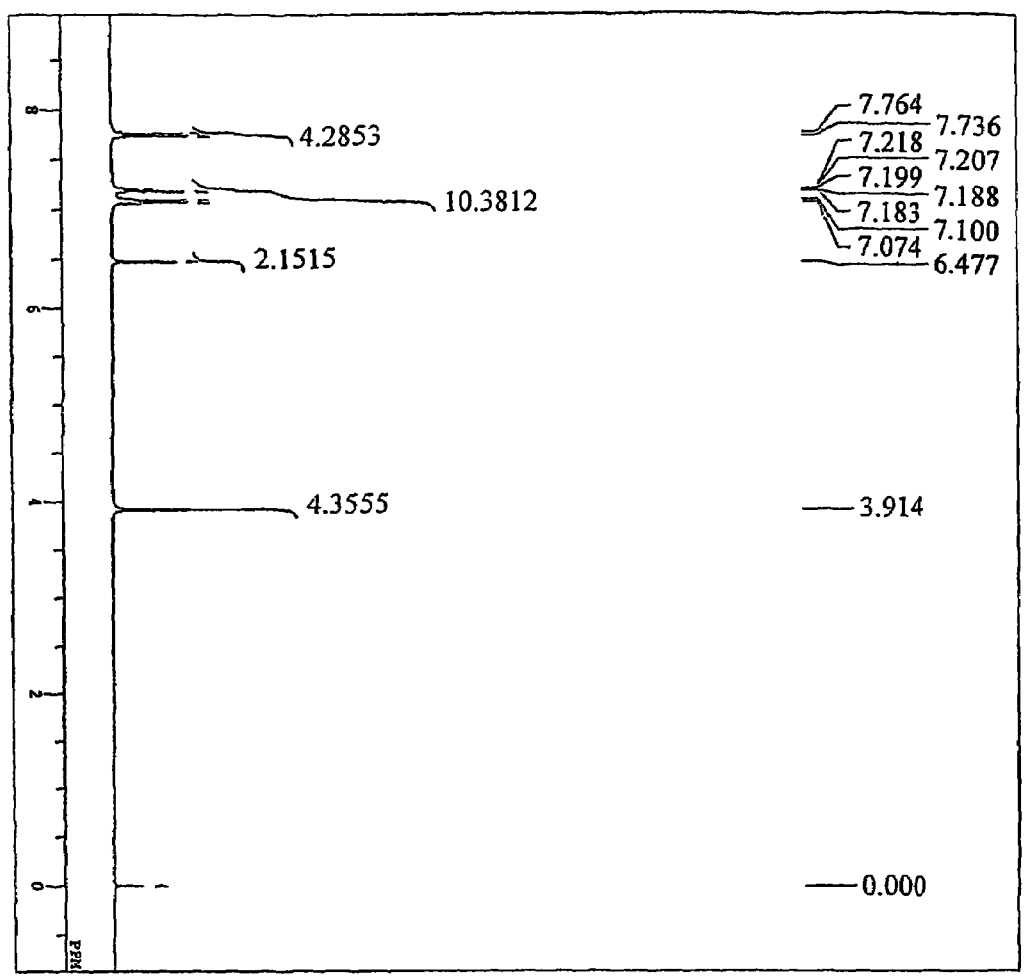
FIG. 3 shows the results of NMR spectrum analysis of Compound (b) obtained in Example 2.
Figure 4:
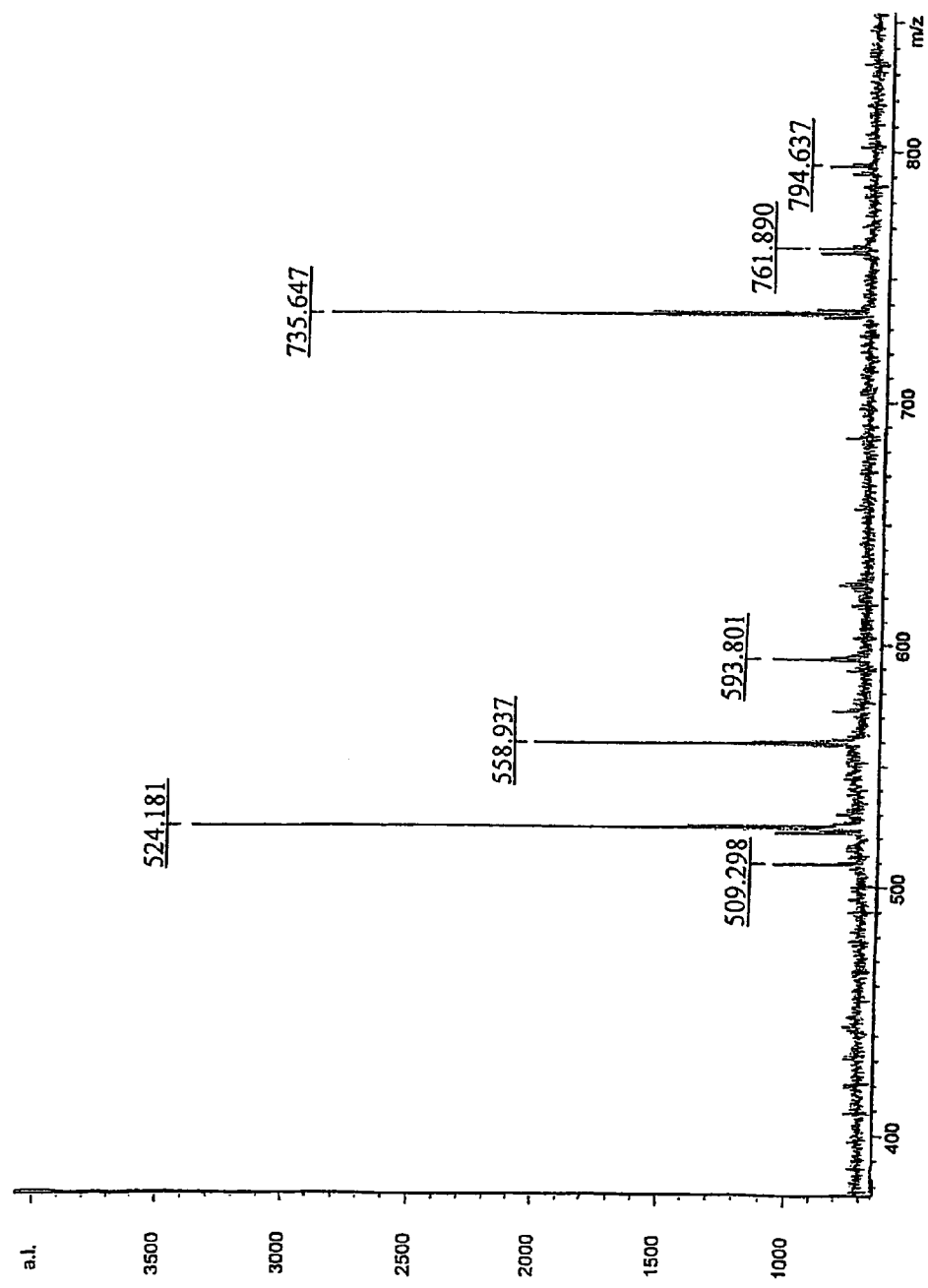
FIG. 4 shows the results of TOF/MS spectrum analysis of Compound (b) obtained in Example 2.

FIG. 2 shows the results of HPLC analysis of Compound (b), FIG. 3 shows the results of NMR analysis thereof, and FIG. 4 shows the results of TOF/MS spectrum analysis thereof.

EXAMPLE 3

The following is an embodiment of a process for synthesizing a compound represented by formula (1).

The First Step

The following is the first step.

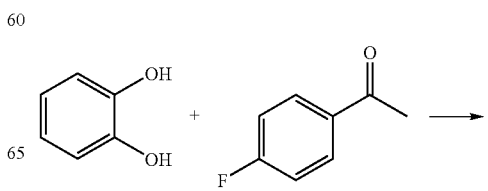

-continued

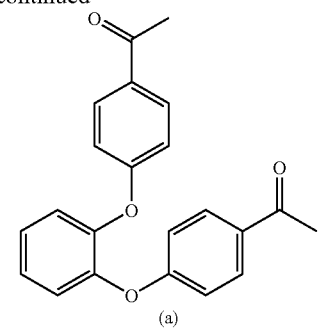

(a)

Materials
(1) 1,2-Dihydroxybenzene
(2) 4'-Fluoroacetophenone

Process of Synthesis

Materials (1) and (2) were allowed to react with each other in the presence of potassium carbonate dissolved in a solvent, i.e., N,N-dimethylacetamide, to obtain Compound (a).

The Second Step

The following is the second step.

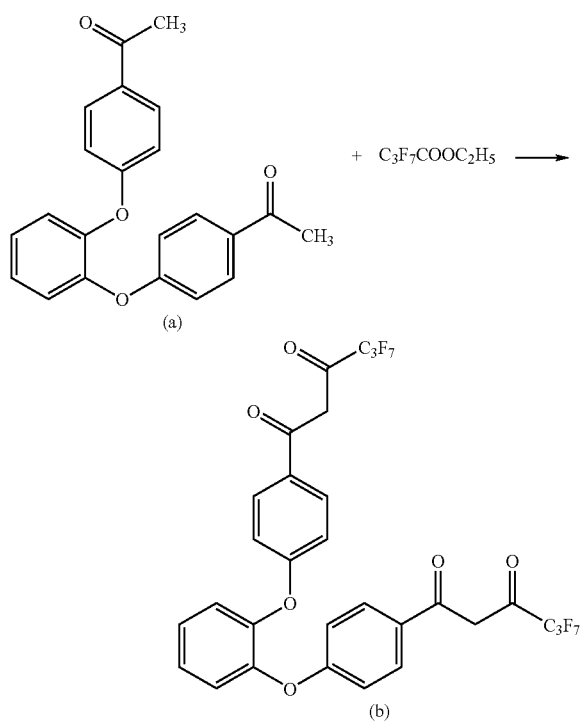

Materials
(1) Compound (a): 1.75 g
(2) Anhydrous diethyl ether: 40 ml
(3) Sodium methoxide: 1.36 g
(4) $C_3F_7COOC_2H_5$: 3.67 g Process of Synthesis Materials (1) and (2) were mixed together, the mixture was allowed to cool, and material (3) was added thereto. Further, 10 ml of a diethyl ether solution of material (4) was added dropwise thereto. The mixture was allowed to cool and stirred for 1 hour. Diethyl ether was added thereto, the pH level was adjusted to 4 with the aid of dilute hydrochloric acid, and the resultant was washed with water and saturated saline in that order. The resultant was dried over anhydrous sodium sulfate, and the solvent was removed by distillation under reduced pressure. Thus, 3.87 g of reddish-brown paste was obtained. This paste was purified by wet column chromatography (solvent: hexane/ethyl acetate=4/1), and 2.69 g of reddish-brown paste was obtained.

EXAMPLE 4

A luminous compound comprising the compound of the present invention was prepared. TTA (4,4,4-trifluoro-1-(2-thienyl)-1,3-butanedione) and BFA (4,4,4-trifluoro-1-phenyl-1,3-butanedione) were purchased from Dojindo Laboratories. Synthesis of BHHT (4,4'-bis(1",1", 1",2",2",3",3"-heptafluoro-4",6"-hexanedion-6"-yl)-o-terphenyl) was carried out in reference to JP-A-09-241233 and Yuan and Matsumoto (Analytical Chemistry, 1998, 70, pp. 596–601).

Figure 5:
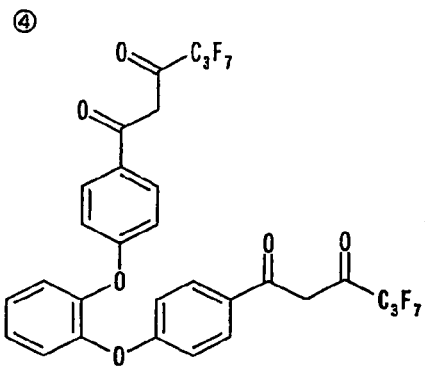
FIG. 5 shows the compounds of the present invention used in examples 5 to 7 and other β-diketone (1,3-dione) compounds.
Figure 5:
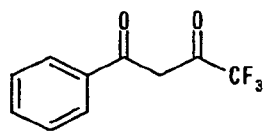
Figure 5:
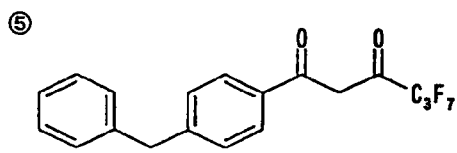
Figure 5:
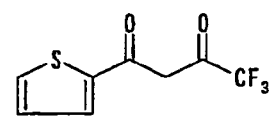
Figure 5:
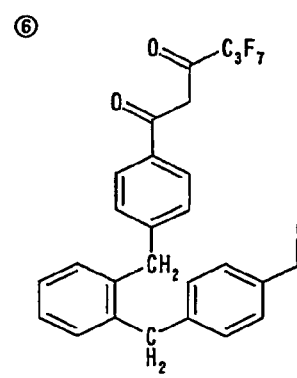
Figure 5:
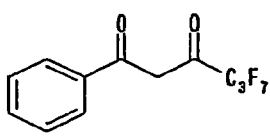
Figure 5:
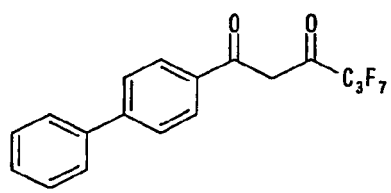
Figure 5:
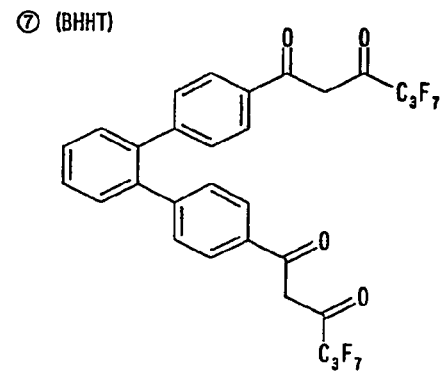
Figure 5:
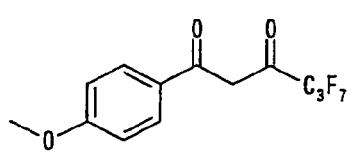

FIG. 5 shows structural formulae of these compounds.

EXAMPLE 5

A compound shown in FIG. 5 comprising the compound of the present invention was dissolved in acetonitrile (Wako Pure Chemical Industries, Ltd.) to a concentration of $10^{-4}$ mol/ml or $10^{-5}$ mol/ml, and the solution was further diluted to $10^{-10}$ mol/ml by 10-fold serial dilution. A solution of this compound ($10^{-7}$ mol/ml) was subjected to absorption spectrum analysis using a spectrophotometer U-3300 (Hitachi High-Technologies). Further, a solution of the aforementioned compound ($10^{-10}$ mol/ml) was mixed with an aqueous solution comprising 0.2 mM europium chloride hexahydrate ($EuCl_3.6H_2O$, Wako Pure Chemical Industries, Ltd.), 0.2 mM TOPO (tri-n-octylphophine oxide, Dojindo Laboratories), and 1% Triton X-100 (Sigma) at the mixing ratio of 1:9, and the resulting mixture was incubated at 42° C. for 2 hours. 0.1 ml of the incubated solution was dispensed to wells of a 96-well flat bottom microtiter plate (Nunc), the plate was irradiated with excitation light at approximately 340 nm, and fluorescence at approximately 615 nm, which had been emitted 0.2 msec to 0.8 msec after the irradiation with the excitation light, was measured using a time-resolved assay apparatus (Hitachi High-Technologies). Further, a similar solution was subjected to the excitation spectrum analysis using a fluorescence spectrometer F-4010 (Hitachi High-Technologies).

Figure 6:
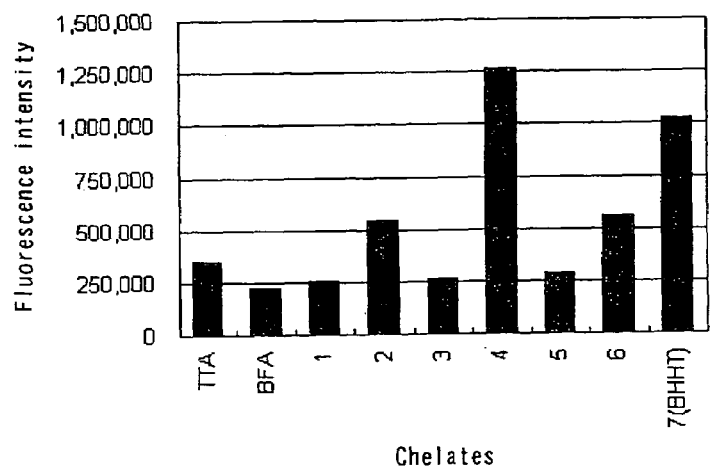
FIG. 6 is a table and a graph showing: the fluorescent signals obtained for the compounds of the present invention with the use of an apparatus for time-resolved assay; the maximal excitation wavelengths for the excitation spectra; and the maximal absorption wavelengths for the absorption spectra.

FIG. 6 shows the results of these analyses. Compound 4 was found to be useful as a fluorophore because it exhibited the highest signal intensity by the assay conducted using a time-resolved assay apparatus and the peak intensity thereof was the highest as a result of the fluorescence spectrum analysis and the absorption spectrum analysis. Compound 6 comprises $CH_2$ denoted by X between phenylene and a carbocyclic ring denoted by Y. This makes the formation of a conjugated system involving 3 carbocyclic rings difficult. Accordingly, signals seem to be increased with the number of compound 1 structures.

EXAMPLE 6

The solution of the compound obtained in Example 5 (0.1 ml, $10^{-11}$ mol/ml) was dispensed to wells of a microtiter plate, the plate was irradiated with excitation light at approximately 340 nm, assay was initiated using a time-resolved assay apparatus 0.1, 0.2, 0.3 . . . 0.8, 0.9, and 1.0 msec after the irradiation of the excitation light, the values representing the emitted signals observed over a period of 0.1 msec following the initiation were dotted in the drawing, and these dots were connected with a line.

Figure 7:
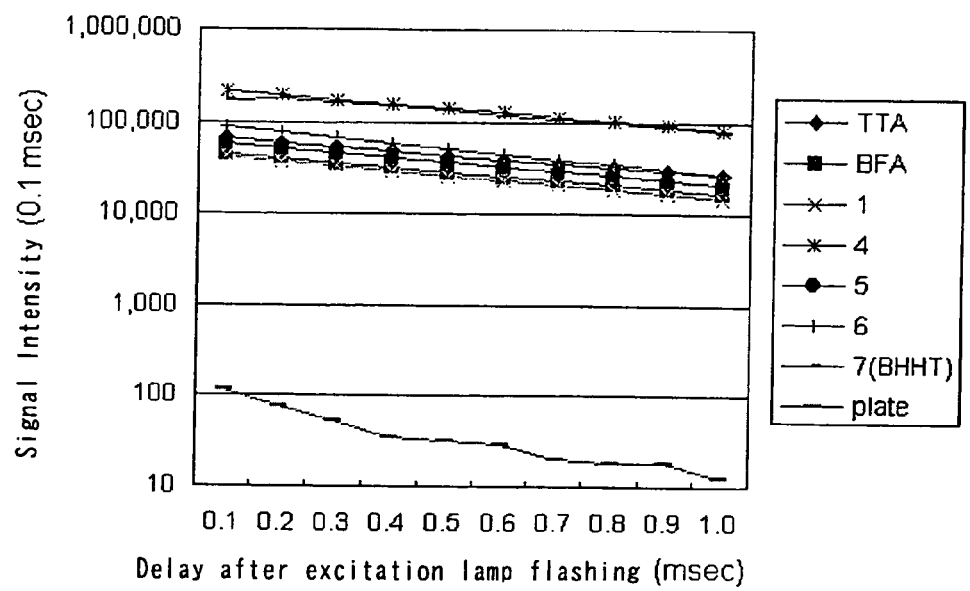
FIG. 7 shows the fluorescence decay curves for the compounds of the present invention.

FIG. 7 shows the results thereof. The compounds of the present invention were found to be capable of maintaining fluorescence for a sufficiently long period of time. Fluorescent signals exhibited the longest half-lives particularly as to Compound 4.

EXAMPLE 7

Assay of α-fetoprotein (AFP)

Assay was carried out according to Yuan and Matsumoto (Analytical Chemistry, 1998, 70, pp. 596–601).

(1) Labeling of AFP Antibody with Biotin (in Accordance with the Producer's Manual for Sulfo-NHS-LC-biotin, Pierce)

An anti-human AFP antibody (1 mg, DACO Immunoglobulins) was dissolved in 1 ml of phosphate buffer saline (PBS, pH, 7.4). Sulfo-NHS-LC-biotin (0.062 mg) was added thereto, and the mixture was allowed to stand in an ice bath for 2 hours. Thereafter, a PD-10 column (Pharmacia) was used to elute and collect an antibody fraction with the aid of PBS, and unbound Sulfo-NHS-LC-biotin was removed. Sodium azide was added to the biotin-labeled antibody solution to account for 0.1% of the solution, and the resultant was stored at 4° C.

(2) Introduction of Chlorosulfonyl into the Compound of Example 4

Chlorosulfuric acid (Wako Pure Chemical Industries, Ltd.) was added to a compound shown in FIG. 5 in an amount of 0.2 ml relative to 0.1 mmol of the compound shown in FIG. 5. The mixture was stirred at room temperature for 7 hours, and the reaction solution was added dropwise to 4 ml of pure water (in an ice bath) while stirring. The resulting precipitate was centrifuged and washed three times with pure water. Thereafter, the precipitate was vacuum dried for 45 hours.

(3) Labeling of a Compound with Streptavidin

Streptavidin (SA, $10^{-5}$ mmol, Chemicon International) was dissolved in 4 ml of 0.1M carbonate buffer (pH 9.1). The compound mentioned in (2) above ($10^{-3}$ mmol) was dissolved in 40 μl of ethanol, and the resultant was added dropwise to a solution of SA. The mixed solution was stirred at room temperature for 1 hour and then thoroughly dialyzed with an aqueous solution of 0.1 M $NaHCO_3$ containing 0.05% sodium azide. After the dialysis, the pH level was adjusted to 6.8 with the aid of 1M HCl, the total amount was brought to 6 ml, and BSA was added thereto to account for 0.1% of the mixture. The resultant was diluted 300-fold with a 0.05M Tris-HCl buffer (pH 7.8) containing $10^{-7}$ M $EuCl_3.6H_2O$, 1% BSA, and 0.1% sodium azide, heated at 56° C. for 2 hours, and then subjected to the reaction.

(4) Coating of a Microtiter Plate with an Anti-AFP Antibody

An anti-human AFP antibody (100 μl, Nippon Biotest Laboratories Inc.) diluted to 5 μg/ml with the aid of 0.1M carbonate buffer (pH 9.6) was dispensed to the wells of a microtiter plate, and the plate was allowed to stand at 4° C. overnight for coating. Thereafter, the plate was washed with 0.05% Tween 20-containing physiological saline, 100 μl of carbonate buffer (pH 9.1) containing 1% BSA and 2% sucrose was added, and the resultant was allowed to stand at 37° C. The plate was washed with 0.05% Tween 20-containing physiological saline (Sigma) 1 hour later and then stored at −20° C.

(5) Implementation of Immunoassays

A human AFP standard preparation (DACO Immunoglobulins) was subjected to a 10-fold serial dilution with PBS containing 1% BSA, and 50 μl thereof was added to each well of a microtiter plate. The plate was shaken at 37° C. for 1 hour and then washed with 0.05% Tween 20-containing physiological saline. Thereafter, the biotin-labeled anti-AFP antibody obtained in (1) was diluted to 1 μg/ml with the aid of 1% BSA-containing physiological saline, and 50 μl thereof was dispensed to each well. The plate was shaken at 37° C. for 1 hour and then washed with 0.05% Tween 20-containing physiological saline. Thereafter, 50 μl of the streptavidin-labeled compound described in the above (3) was dispensed to each well.

The plate was allowed to stand at room temperature for 30 minutes and then washed with 0.05% Tween 20-containing physiological saline. The microtiter plate was subjected to the analysis of the amount of emitted light using a time-resolved assay apparatus.

Figure 8:
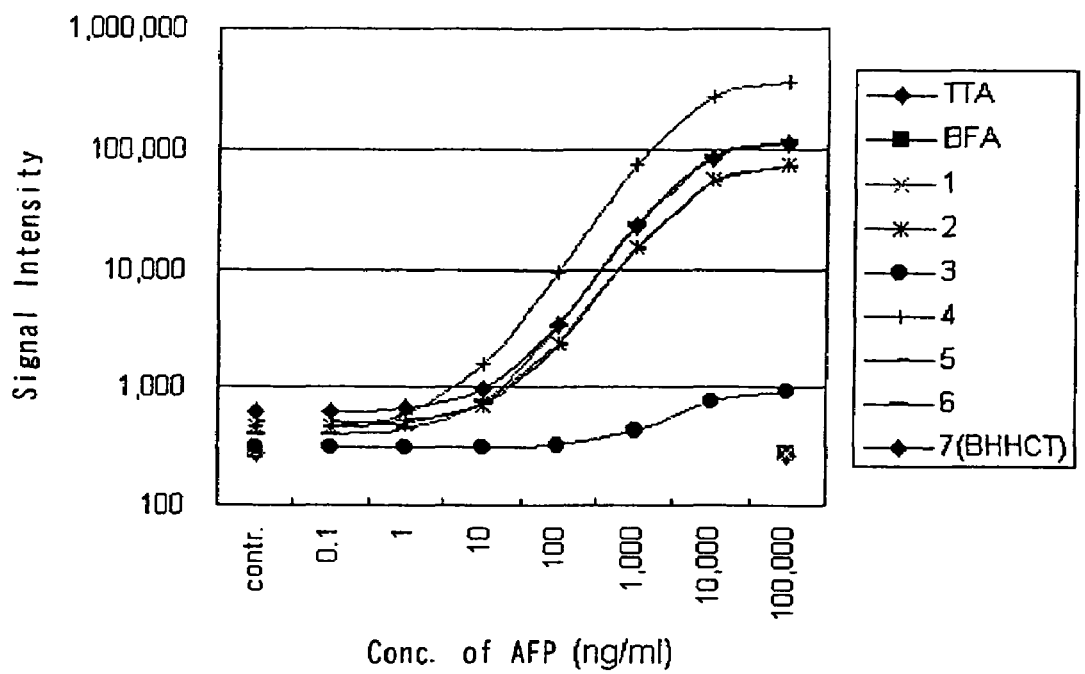
FIG. 8 shows the calibration curves for α-fetoprotein (AFP) obtained by using the compounds of the present invention as labels.
Figure 9:
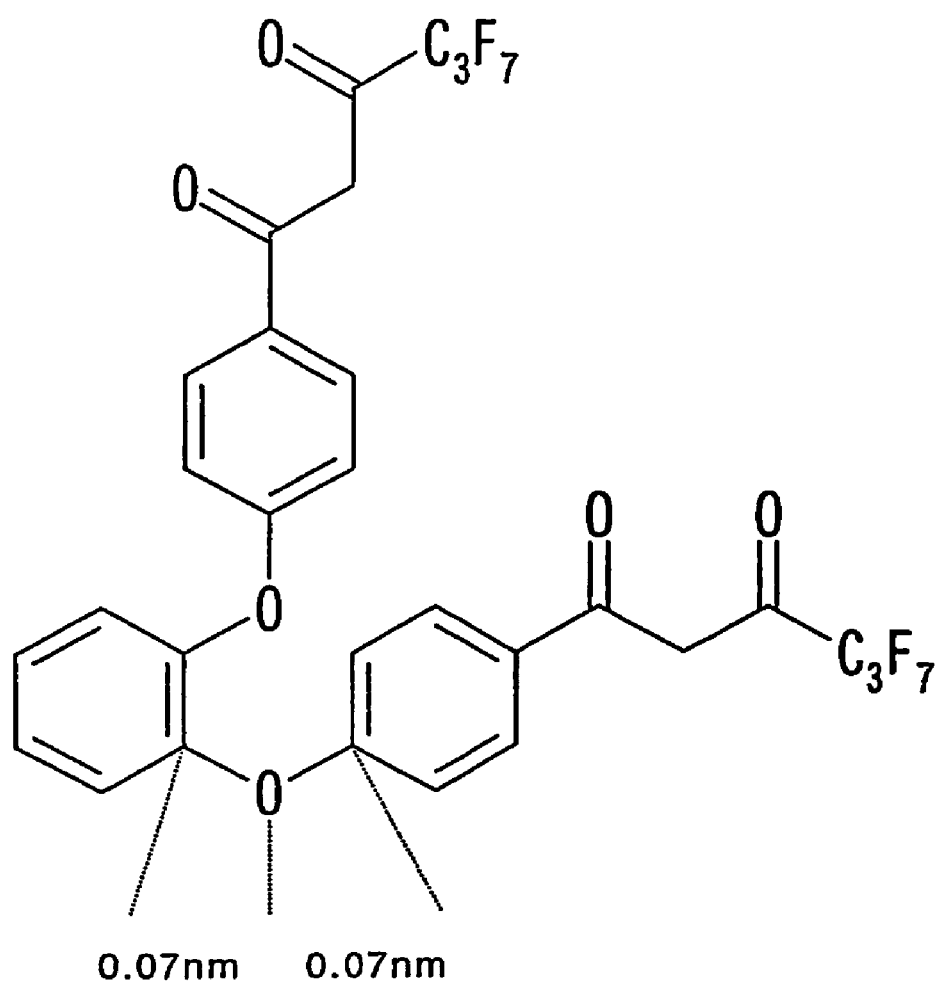
FIG. 9 shows the distinctive features of the present invention with reference to an embodiment of the compound of the present invention.

FIG. 8 shows the results thereof. As is apparent from the drawing, the compounds of the present invention can be efficiently used in immunoassays. In the case of Compound 4, a good calibration curve was produced, and the minimal detection sensitivity attained based thereon was the best value among other compounds, which had been simultaneously examined. A relatively good calibration curve and minimal detection sensitivity were obtained in the case of Compound 6. Although this compound did not exhibit large signals in Example 6, this compound had a good binding property of a reactive group (in this case, chlorosulfonyl residue) and a highly stable trapping property for europium ions at the β-diketone site. Thus, relatively good results were obtained in antigen-antibody reactions.

In the case of Compound 1, TTA, and BFA having a carbocyclic or heterocyclic ring, reactive groups (in this case, chlorosulfonyl residues) did not bind, nor were the europium ions existing in the β-diketone site stably sustained. Thus, no signal indicating antigen-antibody reactions was obtained.

EXAMPLE 8

An embodiment of the compounds of the present invention, i.e., Compound 4 shown in FIG. 5, is examined.

Placement of O denoted by X between phenylene and a carbocyclic ring denoted by Y enlarges the distance between the $C_3F_7$ or β-diketone site and the R site. This makes the compound less susceptible to the electronic absorption effects at the $C_3F_7$ and β-diketone sites and facilitates the introduction of reactive groups. Accordingly, conjugates thereof with an amino acid, peptide, protein, or nucleic acid can be more efficiently obtained.

Similarly, when the compound is bound to solid phase carriers such as amino acids, peptides, proteins, nucleic acids, or plastic particles via a reactive group through placement of O denoted by X, the compound becomes less susceptible thereto at the β-diketone site. This enables rare earth ions to be sustained more effectively and stably. Thus, rare earth ions can form better coordinate bonds with the β-diketone site, which assures the emission of fluorescence or phosphorescence when irradiated with adequate excitation light.

Further, placement of O denoted by X enables more flexible placement of a ligand at the $C_3F_7$ site, the β-diketone site, and the carbocyclic ring subsequent thereto, thereby forming a more stable complex with rare earth ions.

EXAMPLE 9

Compound 4 shown in FIG. 5 was labeled with BSA. Chlorosulfonyl was introduced in accordance with the process described in (2) of Example 7. Labeling was carried out according to Yuan and Matsumoto (Analytical Chemistry, 1998, 70, pp. 596–601).

A solution of DMF (N,N-dimethylformamide, 0.08 ml) containing 1.5 mg of Compound 4 to which chlorosulfonyl had been introduced was added to 0.4 ml of 0.1M carbonate buffer (pH 9.3) containing 2 mg of BSA while stirring. After the mixture was stirred at room temperature, a BSA fraction labeled with the compound was sampled using a PD-10 column. In this case, an aqueous solution of 0.05M $NH_4HCO_3$ (pH 8.0) was used as an eluate.

The sampled fraction was diluted with a 0.05M Tris-HCl buffer (pH 7.8) containing $10^{-7}M$ $EuCl_3.6H_2O$, 1% BSA, and 0.1% sodium azide, and the diluted product was heated at 56° C. for 2 hours.

Figure 10:
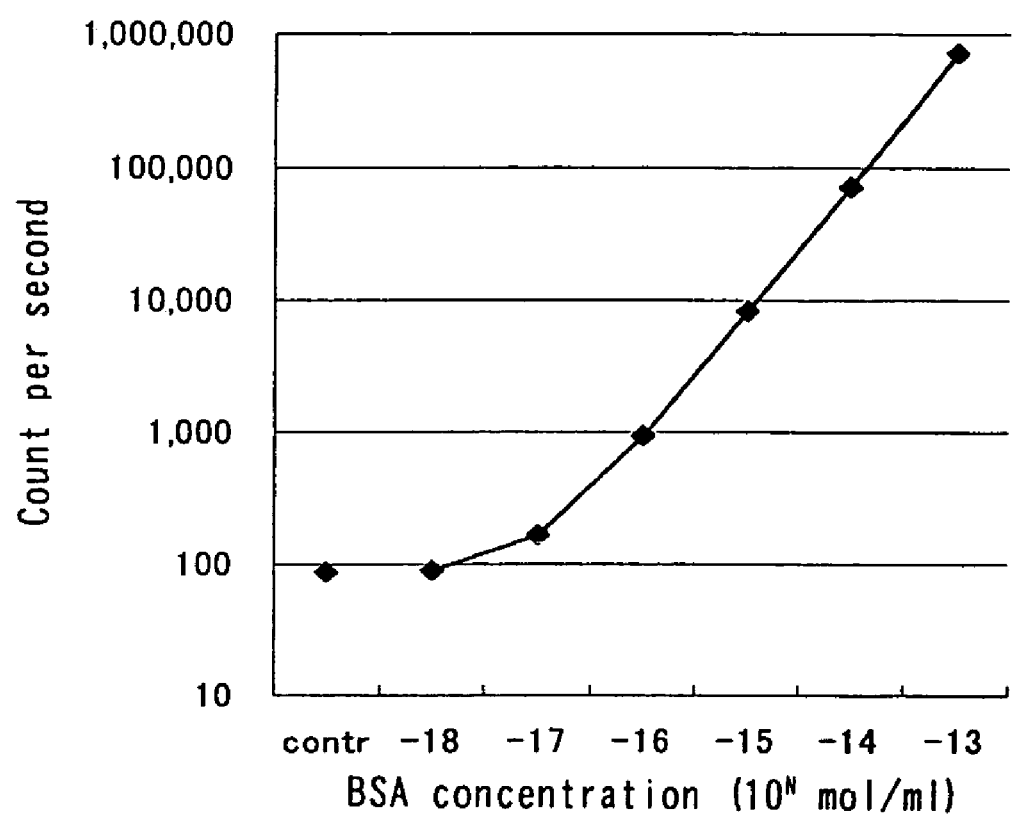
FIG. 10 shows the calibration curves for the europium-labeled bovine serum albumin (BSA) according to the present invention.

Europium-labeled BSA was subjected to a 10-fold serial dilution with the aid of a 0.1M Tris-HCl buffer (pH 9.1) containing 0.05% Tween 20 and 0.05% sodium azide, and the amount of emitted light was measured with a time-resolved assay apparatus. FIG. 10 shows the results thereof. As is apparent from the drawing, the compounds of the present invention can be efficiently used as labels.

EXAMPLE 10

An example of immunoassay using the compound of the present invention (Compound 4 shown in FIG. 5) is hereafter provided.

(1) Labeling of an Anti-Human CRP (C-Reactive Protein) Antibody with Biotin

The anti-human CRP antibody was labeled with biotin in accordance with the process described in (1) of Example 7.

(2) Preparation of SA-labeled Form

In accordance with the process described in (3) of Example 7, an SA-labeled form of Compound 4 shown in FIG. 5 was prepared and europium was further added thereto.

(3) Coating of a Microtiter Plate with an Anti-Human CRP Antibody

In accordance with the process described in (4) of Example 7, a microtiter plate on which the anti-human CRP antibody had been immobilized was prepared.

(4) Implementation of Immunoassay

A human CRP standard preparation was subjected to a 10-fold serial dilution with 1% BSA-containing physiological saline, and 50 μl thereof was added to each well of the microtiter plate. After the plate was shaken at 37° C. for 1 hour, the plate was washed with 0.05% Tween 20-containing physiological saline. Thereafter, the biotin-labeled anti-human CRP antibody obtained in (1) was diluted to 1 μg/l with the aid of 1% BSA-containing physiological saline, and 50 μl thereof was dispensed to each well. After the plate was shaken at 37° C. for 1 hour, the plate was washed with 0.05% Tween 20-containing physiological saline. Thereafter, the europium-labeled SA prepared in (2) was diluted with 1% BSA-containing physiological saline, and 50 μl thereof was fractioniated to each well.

After the plate was allowed to stand at room temperature for 30 minutes, the plate was washed with 0.05% Tween 20-containing physiological saline. The microtiter plate was subjected to the measurement of the amount of light emission with a time-resolved assay apparatus.

Figure 11:
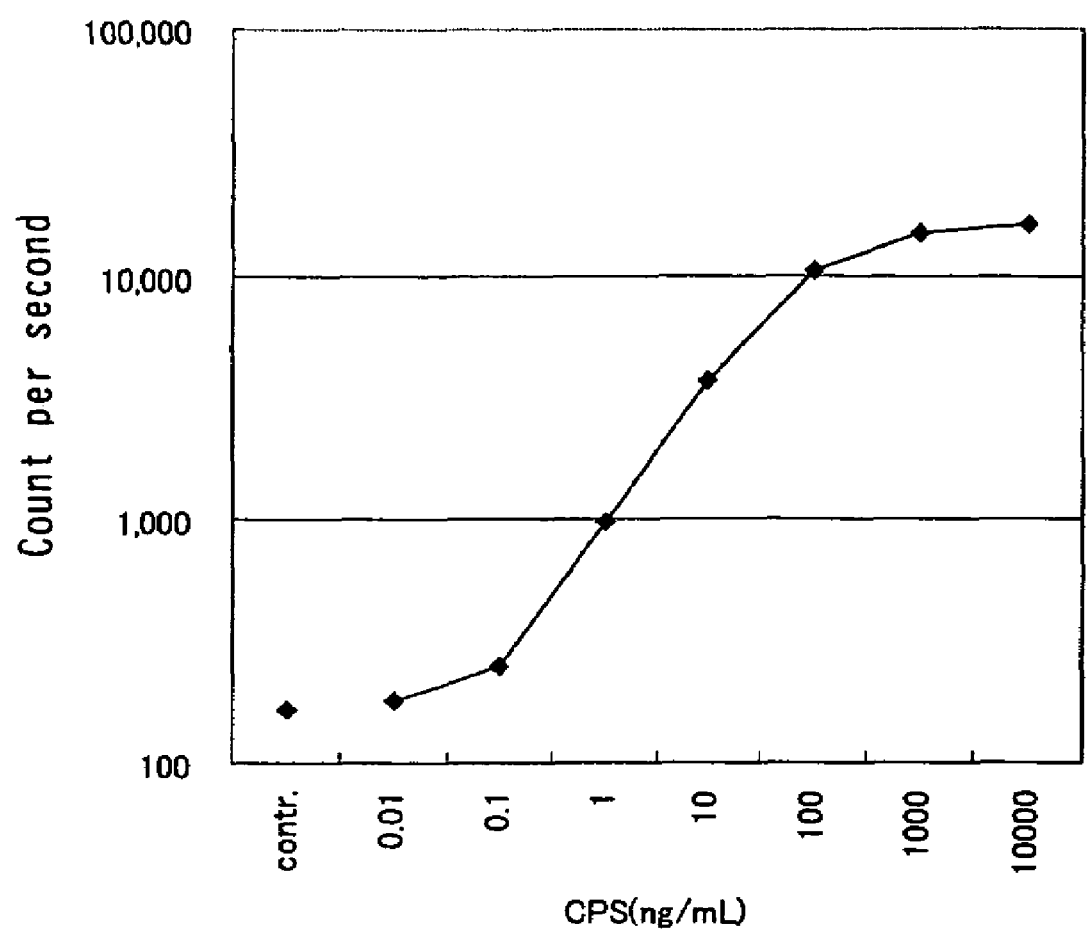
FIG. 11 shows the assay results for human C-reactive proteins (CRP) according to the present invention.

FIG. 11 shows the results thereof. As is apparent from the drawing, Compound 4 shown in FIG. 5 can be efficiently used as a label in immunoassay.

Industrial Applicability

The present invention provides (1) a novel compound that easily forms a complex and (2) a novel compound that can be easily reacted with a protein and the like. Further, the present invention enables the effective use of a label in immunoassay, nucleic acid assay, and other assay techniques.

The invention claimed is:

1. A compound represented by formula (I):

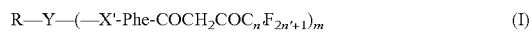

wherein:

R is selected from the group consisting of hydrogen, alkyl, phenyl, and moieties of the formulae:

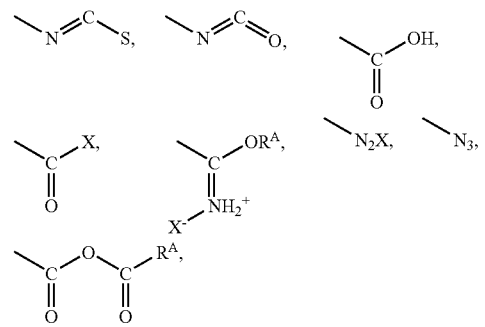

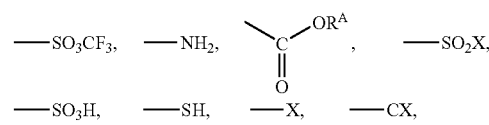

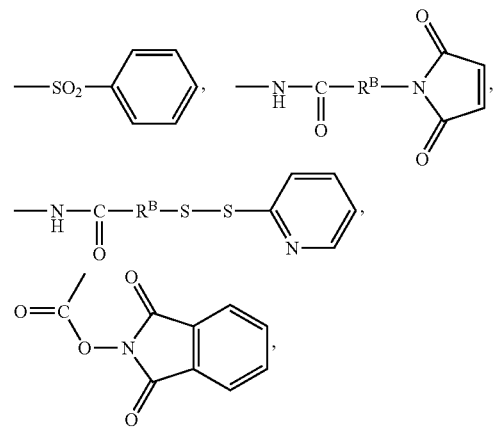

23

[Structures shown:]

—(CH₂)ₚ—C(=O)—O—N(succinimidyl),

—C(=O)—N(imidazolyl),

—NH—C(=O)—(CH₂)q—C(=O)—O—N(succinimidyl),

—(CH₂CH₂O)ₙ—C(=O)—CH₂—C(=O)—O—(2,5-dioxocyclopentyl), and

>N—O—(CH₂CH₂O)ₙ—C(=O)—CH₂—C(=O)—O—(2,5-dioxocyclopentyl) (with S(=O)₂ group)

wherein:
X is selected from the group consisting of halide, —OSO₃CH₃, —OSO₂F, —OSO₂CF₃, —SO₂C₄F₉, and

—OSO₂—C₆H₄—CH₃;

$R^A$ is selected from the group consisting of alkyl, alkenyl, aryl, and aralkyl;
$R^B$ is selected from the group consisting of alkylene, arylene, and aralkylene;
p is an integer from 0 to 5;
q is an integer from 2 to 10; and
n is an integer from 1 to 20;
n' is an integer from 1 to 5;
m is 1, 2, or 3;
in the case where m is 1:
  Phe is 1,4-phenylene;
  Y is selected from the group consisting of $CH_2$, a carbocyclic ring, and a heterocyclic ring;
  in the case where Y denotes $CH_2$,
    X' is selected from the group consisting of S, NH, $OCH_2$, CONH, and NHCO; and
  in the case where Y denotes a carbocyclic ring or a heterocyclic ring,
    X' is selected from the group consisting of O, S, NH, $CH_2$, $OCH_2$, CONH, and NHCO;
and in the case where m is 2 or 3:
  Phe is phenylene;

24

Y is selected from the group consisting of $CH_2$, a carbocyclic ring, and a heterocyclic ring;
  X' is selected from the group consisting of O, S, NH, $CH_2$, $OCH_2$, CONH, and NHCO.

2. The compound of claim 1 represented by the formula:

[Structure with two phenyl–O–C(=O)–CH₂–C(=O)–* groups connected through a central benzene ring bearing R, with both ether linkages]

wherein * denotes $C_{n'}F_{2n'+1}$ (wherein n' is an integer between 1 and 5) and R is as defined in claim 1.

3. The compound of claim 1 represented by the formula:

[Analogous structure with –CH₂– linkages instead of –O– linkages connecting the phenyl groups to the central R-substituted benzene ring]

wherein * denotes $C_{n'}F_{2n'+1}$ (wherein n' is an integer between 1 and 5) and R is as defined in claim 1.

4. The compound of claim 1 represented by the formula:

[Analogous structure with –NH– linkages connecting the phenyl groups to the central R-substituted benzene ring]

wherein * denotes $C_{n'}F_{2n'+1}$ (wherein n' is an integer between 1 and 5) and R is as defined in claim 1.

5. The compound of claim 1 represented by the formula:

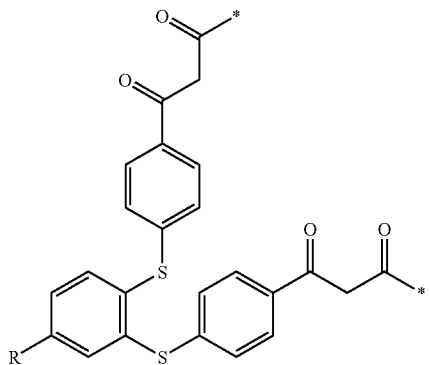

wherein * denotes $C_{n'}F_{2n'+1}$ (wherein n' is an integer between 1 and 5) and R is as defined in claim 1.

6. The compound of claim 1 represented by the formula:

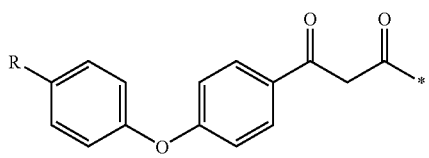

wherein * denotes $C_{n'}F_{2n'+1}$ (wherein n' is an integer between 1 and 5) and R is as defined in claim 1.

7. The compound of claim 1 represented by the formula:

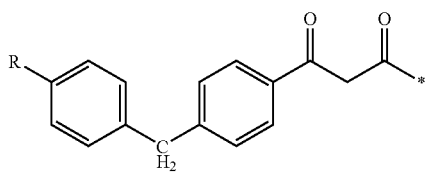

wherein * denotes $C_{n'}F_{2n'+1}$ (wherein n' is an integer between 1 and 5) and R is as defined in claim 1.

8. The compound of claim 1 represented by the formula:

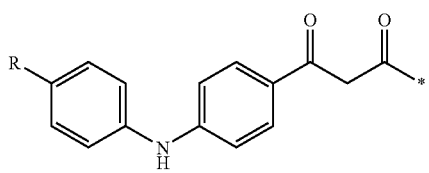

wherein * denotes $C_{n'}F_{2n'+1}$ (wherein n' is an integer between 1 and 5) and R is as defined in claim 1.

9. The compound of claim 1 represented by the formula:

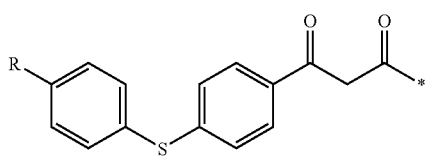

wherein * denotes $C_{n'}F_{2n'+1}$ (wherein n' is an integer between 1 and 5) and R is as defined in claim 1.

10. The compound of claim 1 represented by the formula:

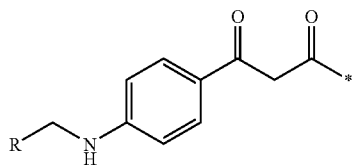

wherein * denotes $C_{n'}F_{2n'+1}$ (wherein n' is an integer between 1 and 5) and R is as defined in claim 1.

11. The compound of claim 1 represented by the formula:

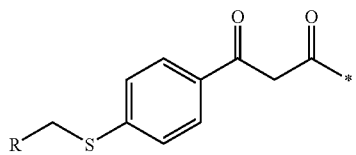

wherein * denotes $C_{n'}F_{2n'+1}$ (wherein n' is an integer between 1 and 5) and R is as defined in claim 1.

12. The compound of claim 1 represented by the formula:

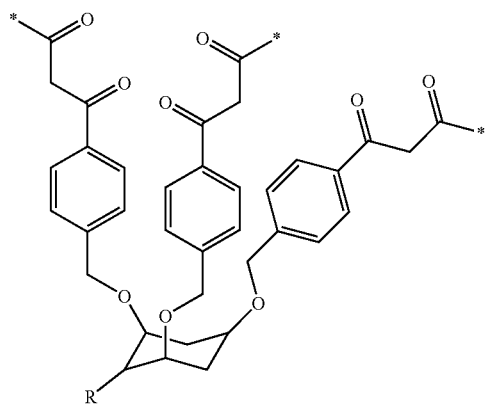

wherein * denotes $C_{n'}F_{2n'+1}$ (wherein n' is an integer between 1 and 5) and R is as defined in claim 1.

13. The compound of claim 1 represented by the formula:

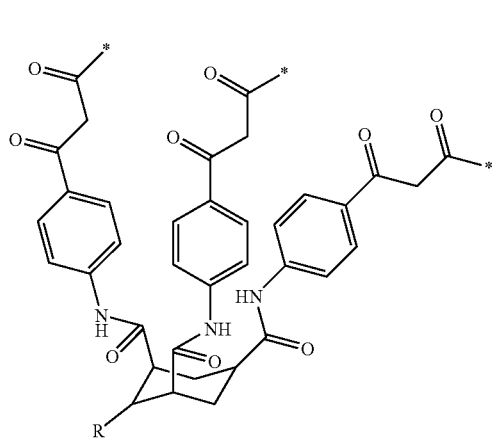

wherein * denotes $C_{n'}F_{2n'+1}$ (wherein n' is an integer between 1 and 5) and R is as defined in claim 1.

14. A fluorescent complex comprising the compound of claim 1 and a rare earth ion.

15. A labeling reagent comprising the compound of claim 1 or the fluorescent complex of claim 14.

16. The labeling reagent of claim 15 for immunoassays or nucleic acid assays.

17. A method for labeling a protein, peptide, amino acid, nucleic acid, or nucleotide utilizing the labeling reagent of claim 15.

* * * * *